United States Patent
Barthelet et al.

(10) Patent No.: US 10,428,282 B2
(45) Date of Patent: Oct. 1, 2019

(54) METHOD FOR SIMULTANEOUSLY ELIMINATING ISOBUTANAL AND ETHANOL FROM OLEFINIC FEEDSTOCKS BY ADSORPTION ON A POROUS REFRACTORY OXIDE-BASED MATERIAL

(71) Applicants: TOTAL RESEARCH & TECHNOLOGY FELUY, Seneffe (BE); IFP Energies nouvelles, Rueil-Malmaison (FR)

(72) Inventors: Karin Barthelet, Lyons (FR); Emmanuelle Bracco, Condrieu (FR); Vincent Coupard, Lyons (FR); Nikolai Nesterenko, Nivelles (BE)

(73) Assignees: TOTAL RESEARCH & TECHNOLOGY FELUY, Seneffe (BE); IFP Energies nouvelles, Rueil-Malmaison (FR)

( * ) Notice: Subject to any disclaimer, the term of this patent is extended or adjusted under 35 U.S.C. 154(b) by 0 days.

(21) Appl. No.: 16/217,887

(22) Filed: Dec. 12, 2018

(65) Prior Publication Data
US 2019/0177624 A1    Jun. 13, 2019

(30) Foreign Application Priority Data
Dec. 13, 2017  (FR) .................................. 17 62091

(51) Int. Cl.
| | | |
|---|---|---|
| C10G 53/08 | (2006.01) | |
| C07C 7/12 | (2006.01) | |
| C07C 7/00 | (2006.01) | |

(52) U.S. Cl.
CPC .............. *C10G 53/08* (2013.01); *C07C 7/005* (2013.01); *C07C 7/12* (2013.01); *C10G 2300/1092* (2013.01); *C10G 2300/202* (2013.01); *C10G 2400/20* (2013.01)

(58) Field of Classification Search
None
See application file for complete search history.

(56) References Cited

U.S. PATENT DOCUMENTS

| | | | |
|---|---|---|---|
| 9,233,886 B2 | 1/2016 | Adam | |
| 9,260,355 B2 * | 2/2016 | Vermeiren | ................ C07C 1/24 |
| 2008/0015395 A1 * | 1/2008 | D'amore | .................... C07C 1/24 568/697 |

FOREIGN PATENT DOCUMENTS

EP    2547639 B1    8/2016

OTHER PUBLICATIONS

Search report in corresponding FR 1762091 dated Aug. 3, 2018 (pp. 1-2).

* cited by examiner

*Primary Examiner* — Tam M Nguyen
(74) *Attorney, Agent, or Firm* — Millen, White, Zelano and Branigan, P.C.

(57) ABSTRACT

This invention pertains to a method for purifying an olefinic feedstock that comprises olefins with 4 carbon atoms and impurities including isobutanal, ethanol, and acetone, where said method comprises a pretreatment that comprises a step for eliminating acetone and optionally a step for eliminating the water that is present in said olefinic feedstock, and a step for simultaneously eliminating isobutanal and ethanol by running the feedstock obtained from the pretreatment over at least one fixed bed having at least one adsorbent that comprises at least one porous refractory oxide-based material, optionally impregnated with one or more alkaline or alkaline-earth cations; where said step for simultaneously eliminating isobutanal and ethanol operates at a temperature of between 0 and 200° C., at a pressure of 0.1 to 10 MPa, and with an hourly volumetric flow rate (VVH) of the feedstock on the fixed bed of between 0.1 and 10 $h^{-1}$.

14 Claims, 1 Drawing Sheet

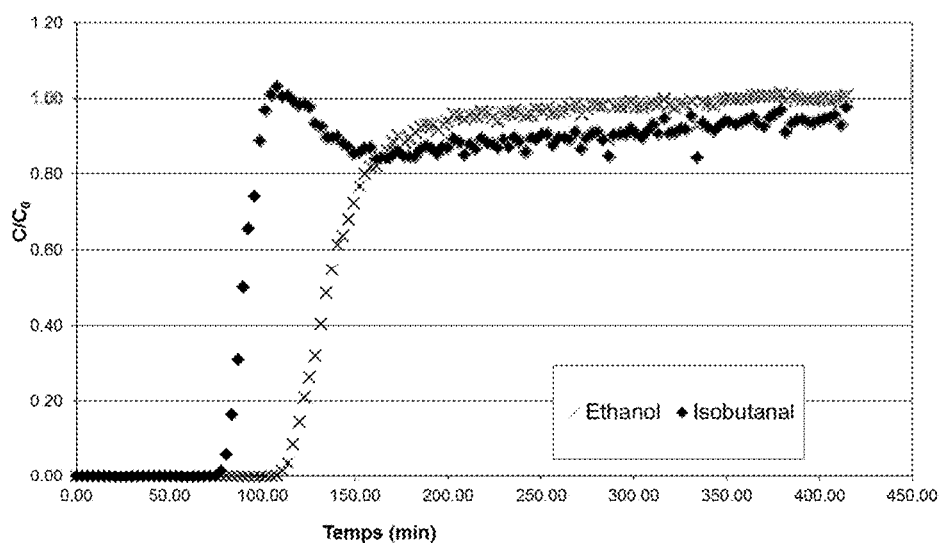

METHOD FOR SIMULTANEOUSLY ELIMINATING ISOBUTANAL AND ETHANOL FROM OLEFINIC FEEDSTOCKS BY ADSORPTION ON A POROUS REFRACTORY OXIDE-BASED MATERIAL

FIELD OF THE INVENTION

This invention pertains to a method for purifying an olefinic feedstock that comprises a step for simultaneously eliminating aldehydes and alcohols that are contained in the olefinic feedstock, where this step is carried out at low temperature (equal to or less than 200° C.) by adsorption on an adsorbent that comprises a porous substrate that is essentially based on a porous refractory oxide, such as alumina. More particularly, the invention pertains to a method for purifying an olefinic feedstock that comprises olefins with 4 carbon atoms and impurities that comprise isobutanal, ethanol, and acetone, where said method comprises a step for simultaneously eliminating isobutanal and ethanol by RUNNING said olefinic feedstock, after being pretreated, over a fixed bed that comprises at least one porous refractory oxide-based material, optionally impregnated with one or more alkaline or alkaline-earth cations. The pretreatment of the olefinic feedstock comprises at least the elimination of the acetone and optionally the water that are present in the olefinic feedstock.

The invention is advantageously applied to the treatment of effluents from the conversion of oxygenated compounds and in particular to the treatment of the effluent obtained from the dehydration of a butanol isomer, especially isobutanol, or a mixture of butanol isomers that comprises isobutanol.

STATE OF THE ART

The butenes that are produced by the dehydration of alcohol, in particular by the dehydration of a butanol isomer, especially isobutanol, or a mixture of butanol isomers that comprises isobutanol, generally contain several hundred ppm by mass of isobutanal, ethanol, and acetone. However, in order to meet the specifications that are levied on butenes, it turns out to be necessary to eliminate them. As a matter of fact, the butenes that are produced may be intended to be sent to a metathesis unit that uses a catalyst that does not tolerate more than 10 ppm by weight of oxygen. Here, "ppm by weight of oxygen" or "oxygen content" is defined to mean the oxygen atom content by mass present in the mixture in question. This oxygen content can be calculated from the composition by mass or molar composition in terms of oxygenated hydrocarbon compounds of the mixture in question.

Patent EP 2 547 639 B1, which describes an alkene metathesis method, explains that numerous pollutants that are present in the metathesis feedstock are responsible for the drop in the catalyst's activity.

In order to achieve very low impurity concentration levels, one of the techniques that is often used is adsorption on a solid that is present in a fixed bed. It is important, however, to find the right adsorbent(s) to make it possible to eliminate all of the impurities that are present.

Patent EP 2 547 639 B1 cites aluminas and zeolites as potential adsorbents. However, no connection is given between the nature of the compounds to be eliminated and the choice of the adsorbent for making effective treatment of the alkenes possible.

The article by C. C. Brunchi et al., Ind. Eng. Chem. Res., 2012, 51, 16697-16708, describes the batch co-adsorption of a mixture of volatile organic compounds (VOC), isobutanal, 2-ethyl-2-hexanal, 2,6-dimethylcyclohexanone, 2,4,6-trimethylphenol, and 2,4,6-trimethylanisole, in toluene. It appears that the NaY zeolite makes it possible to adsorb significant quantities of these different molecules. C. C. Brunchi et al. also show that the capture capacity of zeolite highly decreases when the concentration of compounds in toluene decreases.

The use of this type of solid will make the effectiveness of the method dependent upon the concentration of the feedstock, thereby making the sizing of the purification zone difficult. C. C. Brunchi et al. also evaluated aluminas for the elimination of VOC by adsorption: they show that only butanal can be adsorbed in significant quantities. The other organic compounds' capture capacities for these aluminas are low.

The Applicant has shown that the use in a fixed bed of at least one adsorbent that comprises at least one porous refractory oxide-based material, optionally impregnated with one or more alkaline or alkaline-earth cations, makes it possible to simultaneously eliminate isobutanal and ethanol from olefinic feedstocks that comprise olefins having 4 carbon atoms, from which acetone and optionally water have been eliminated in advance.

This invention thus pertains to a method for purifying an olefinic feedstock that comprises olefins having 4 carbon atoms, in particular a feedstock that is obtained from the dehydration of an isomer of butanol, especially isobutanol, or a mixture of butanol isomers that comprises isobutanol, thereby making it possible to eliminate the isobutanal, acetone, and ethanol impurities contained in amounts of several hundred ppm by mass in said feedstock.

SUMMARY OF THE INVENTION

In particular, this invention pertains to a method for purifying an olefinic feedstock that comprises olefins that have 4 carbon atoms and impurities including isobutanal, ethanol, and acetone, wherein said method comprises:
a) A pretreatment step comprising at least one step for acetone elimination; and
b) A step for simultaneously eliminating isobutanal and ethanol by running the pretreated feedstock obtained from Step a) over at least one fixed bed that has at least one adsorbent that comprises at least one material based on porous refractory oxide,
wherein said Step b) operates at a temperature of between 0 and 200° C., at a pressure of 0.1 to 10 MPa, and with an hourly volumetric flow rate (VVH) of the pretreated feedstock obtained from Step a) on the fixed bed of between 0.1 and 10 $h^{-1}$.

The invention is advantageously applied to the treatment of the effluents from the conversion of oxygenated compounds and in particular to the treatment of the effluent produced by the dehydration of an isomer of butanol, particularly isobutanol, or a mixture of butanol isomers that comprises isobutanol. In particular, the invention applies to the treatment of the effluent obtained from the dehydration of isobutanol by itself or in a mixture with other butanol isomers.

Advantageously, the use of a fixed bed with at least one specific adsorbent, wherein said adsorbent comprises at least one porous refractory oxide-based material, under the specific conditions according to the invention, makes it possible to eliminate simultaneously the isobutanal and ethanol impurities contained in the mixture of butenes that are produced by the dehydration of isobutanol or of a mixture of butanol isomers that comprises isobutanol.

The purification method according to the invention thus makes it possible, due in particular to the use of a fixed bed with a specific adsorbent and optimized conditions, to obtain a content—in terms of oxygen that is indicative of the oxygenated hydrocarbon impurities content in the olefinic mixture obtained from purification—of less than 50 ppm by mass, preferably less than or equal to 30 ppm by mass, preferably less than or equal to 15 ppm by mass, in a preferred manner less than or equal to 10 ppm by mass, and in a very preferred manner less than or equal to 1 ppm by mass. The term "oxygen content" is defined here as the oxygen atom content by mass contained in the mixture in question. This oxygen content can be calculated based on the composition by mass or molar composition in terms of oxygenated hydrocarbon compounds of the mixture in question. Advantageously, the method according to the invention makes it possible to obtain contents by mass in terms of oxygenated hydrocarbon impurities, such as isobutanal, ethanol, and acetone, in the olefinic mixture obtained from purification, which are less than 50 ppm by mass, preferably less than or equal to 30 ppm by mass, preferably less than or equal to 15 ppm by mass, in a preferred manner less than or equal to 10 ppm by mass, and in a very preferred manner less than or equal to 1 ppm by mass.

Unlike adsorbents of the zeolite type, whose selectivity is highly favorable to ethanol, the adsorbent that comprises at least one porous refractory oxide-based material can ensure the treatment of olefin feedstocks that contain isobutanal and ethanol, without the latter hampering the adsorption of the isobutanal.

In the method according to the invention, the adsorbent that comprises at least one porous refractory oxide-based material can undergo multiple regeneration cycles and still retain satisfactory capture capacities for isobutanal and ethanol, thereby providing a real economic advantage.

DESCRIPTION OF THE INVENTION

In the present invention, the term "content of oxygenated hydrocarbon impurities" or "mass content of oxygenated hydrocarbon impurities" of a feedstock or effluent (initial feedstock, olefinic feedstock, or effluent obtained from the method) is defined as the mass of oxygenated hydrocarbon impurities, such as isobutanal, ethanol, and acetone, per unit of mass of the feedstock or effluent in question. An example that can be cited of a common technique for determining the contents of each of the oxygenated hydrocarbon impurities is gas-phase chromatography, which corresponds to determination according to the method UOP 960.

It should be noted that the oxygen of water that is present in dissolved form in the feedstock or the effluent is not taken into account in the content of oxygenated hydrocarbon impurities. The content of water present in dissolved form in the feedstock or the effluent can be determined by a specific technique, for example according to the method of Karl Fischer (cf. Analyse des solvants résidue's dans les produits pharmaceutiques, techniques de l'ingénieur [Analysis of the Residual Solvents in Pharmaceutical Products, Engineer Techniques], P3260 Vol. 1, M. Bauer Oct. 9, 2001).

In the present invention, the term "hourly volumetric flow rate (VVH) of the feedstock on the fixed bed" is defined as the ratio between the hourly volumetric flow rate of the feedstock to be treated and the volume of the reactor.

According to this invention, the expression "between . . . and . . . " means that the boundary values of the interval are included in the range of values described. If this was not the case and the boundary values were not included in the range described, this precision will be provided by this invention.

The present invention consists of a method for purifying an olefinic feedstock that comprises olefins having 4 carbon atoms and impurities including isobutanal, ethanol, and acetone, wherein said method comprises:

a) A pretreatment step that comprises at least one acetone elimination step; and b) A step for simultaneously eliminating isobutanal and ethanol by running the pretreated feedstock obtained from Step a) over at least one fixed bed with at least one adsorbent that comprises at least one porous refractory oxide-based material;

wherein said Step b) operates at a temperature of between 0 and 200° C. and at a pressure of 0.1 to 10 MPa, and with an hourly volumetric flow rate (VVH) of the pretreated feedstock obtained from Step a) on the fixed bed of between 0.1 and 10 $h^{-1}$.

Olefinic Feedstock

The olefinic feedstock that is treated by the purification method according to the invention is a mixture of olefins. This mixture can contain linear or branched olefins or a mixture of linear and branched olefins.

The olefinic feedstock is characterized by its very high olefin content. Said feedstock contains preferably at least 95% by weight and preferably at least 97% by weight of its dry weight in olefins. The high content of olefins imparts to this fraction an especially high reactivity both in the downstream recovery steps and in the transformation or purification steps that it undergoes.

The olefins that are present in the feedstock are compounds mainly having 4 carbon atoms, more particularly butenes, and especially a mixture of n-butenes and isobutene.

The feedstock that is treated according to the invention can also contain non-olefinic compounds, which can include, in addition to water, organic hydrocarbon compounds (impurities). The organic hydrocarbon compounds can be paraffins and dienes, organic oxygenated compounds, among which it is possible to cite aldehydes, ketones, alcohols, acetals, ester ethers, furans, and carboxylic acids.

More particularly, the feedstock that is treated in accordance with the invention comprises olefins having 4 carbon atoms and oxygenated hydrocarbon impurities including isobutanal, ethanol, and acetone.

According to a variant of the invention, the olefinic feedstock is obtained from the conversion of oxygenated compounds. Preferably, the olefinic feedstock treated according to the invention is obtained from the dehydration of isobutanol or a mixture of isomers of butanol that comprises isobutanol. Preferably, the olefinic feedstock treated according to the invention is obtained from the dehydration of an isomer of butanol, in particular isobutanol, or a mixture of isomers of butanol that comprises isobutanol. Typically, the butenes produced by the dehydration of isobutanol or a mixture of isomers of butanol that comprises isobutanol contain several hundred ppm of isobutanal, ethanol, and acetone.

Step a)

According to the invention, the olefinic feedstock undergoes a pretreatment that comprises at least one acetone elimination step. The pretreatment can also comprise a step for elimination of the water that the olefinic feedstock may contain.

The Applicant has discovered that among the impurities that are present in the olefinic feedstock, some are incompatible with the use of a porous refractory oxide-based adsorbent. In particular, the presence of acetone in the feedstock significantly impairs the performance of the adsorbent that comprises at least a porous refractory oxide-based material such as alumina. In point of fact, the acetone reacts with the isobutanal upon contact with the refractory oxide-based material, which includes in particular sites of a basic nature (such as aluminas, MgO, . . . ), to produce heavier compounds that are less well adsorbed and that thus reduce adsorption capacity as well as access to the adsorption sites. It is thus appropriate to eliminate these impurities, in particular acetone, before the feedstock to be treated is passed over the adsorbent that comprises at least one porous refractory oxide-based material, optionally doped.

The pretreatment thus makes it possible to limit or even prevent isobutanal from reacting with acetone (aldolization). The pretreatment also makes it possible to avoid a loss of adsorption capacity on the part of the adsorbent used in Step b), which includes the porous refractory oxide-based material, with respect to isobutanal and ethanol. The pretreatment of the olefinic feedstock, in accordance with Step a), thus makes it possible to optimize the isobutanal and ethanol capture capacity of the adsorbent that comprises the refractory oxide-based material in Step b).

The acetone and optionally the water contained in the olefinic feedstock are eliminated by any method known to one skilled in the art. In particular, acetone can be removed from the feedstock that is to be treated by methods of stripping, distillation, topping, pasteurization, or rectification. The water can be eliminated by, for example, adsorption on a type 3A molecular sieve.

When the water elimination step is integrated into the treatment method according to the invention, said step can be carried out simultaneously with the acetone elimination step. This step can also be carried out before or after the acetone elimination step.

Advantageously, at the output of the pretreatment (Step a), the olefinic feedstock contains less than 10 ppm by mass, preferably less than 1 ppm by mass, of water, and less than 10 ppm by mass, and preferably less than 1 ppm by mass, of acetone. And, more particularly, the feedstock is devoid of water and acetone.

The Porous Refractory Oxide-Based Adsorbent

According to the invention, the purification method comprises running the olefinic feedstock into a reactor that comprises at least one fixed bed with at least one specific adsorbent. The adsorbent according to the invention comprises at least one porous refractory oxide-based material.

The porous refractory oxide-based material is preferably selected from the group that consists of: alumina, silica, titanium oxide, zirconium oxide, magnesium oxide, and mixtures thereof. Preferably, the porous refractory oxide-based material is based on alumina.

The preferred porous refractory oxides have a specific surface area that is measured by the B.E.T. method according to the Standard ASTM D3663, expressed in terms of $S_{BET}$, of advantageously between 30 m²/g and 400 m²/g.

The preferred porous refractory oxides have a total pore volume, which is determined by mercury intrusion according to the Standard ASTM D6761 with a wetting angle of 140° using, for example, a device such as the Autopore III™ model of the Micromeritics™ brand, greater than or equal to 0.05 ml/g and preferably between 0.1 and 1.5 ml/g.

Advantageously, the refractory oxides exhibit macroporosity. More particularly, the preferred porous refractory oxides have a macropore volume, that is, the cumulative volume of pores with a diameter greater than 50 nm, greater than or equal to 0.01 ml/g, preferably between 0.01 and 0.4 ml/g, and in a very preferred manner between 0.05 and 0.2 ml/g. This volume is determined by mercury intrusion according to the Standard ASTM D4284 with a wetting angle of 140° using, for example, a device such as the Autopore III™ model of the Micromeritics™ brand.

The porous refractory oxide-based material is optionally impregnated with one or more alkaline or alkaline-earth cations.

Alkaline cations are cations of elements selected from lithium, sodium, potassium, rubidium, and cesium, and preferably from sodium and potassium. Alkaline-earth cations are cations of elements selected from beryllium, magnesium, calcium, strontium, barium, and radium, preferably from magnesium, calcium, and strontium, and in an even more preferred manner from magnesium and calcium.

Preferably, the porous refractory oxide-based material is impregnated with one or more alkaline or alkaline-earth cations at a level from 0.2% to 40% by weight, preferably from 0.2 to 30% by weight, in a preferred manner from 0.2 to 20% by weight, and in a very preferred manner from 0.2 to 10% by weight, relative to the total weight of the adsorbent after impregnation.

The cation content can be measured by atomic absorption spectroscopy, in particular according to the method described in the work by J. Lynch "Analyse Physico-chimique des catalyseurs industriels—Manual practique de caractérisation" [Physical-Chemical Analysis of Industrial Catalysts—Practical Characterization Manual], Editions Technip, 2001.

The impregnation of the porous refractory oxide-based material can be done by any of the known methods, in particular by immersion or the dry method. In a preferred manner, the alkaline or alkaline-earth cation(s) is (are) dry-impregnated on the porous refractory oxide-based material. Dry impregnation consists in bringing a quantity of porous refractory oxide into contact with a volume of impregnation solution that precisely corresponds to its available pore volume. The alkaline or alkaline-earth cation(s) can be impregnated one or more times.

The precursors of the alkaline or alkaline-earth cations are selected in a preferred manner from among hydroxides, nitrates, and carbonates.

After each impregnation, the impregnated porous refractory oxide-based material that is obtained is dried at a temperature of between 90 and 120° C. for 3 to 12 hours and then optionally calcined under air at a temperature of between 300 and 550° C. for 0.5 to 6 hours. The drying and calcination can be carried out, for example, under nitrogen or under dry or moist air.

Advantageously, the porous refractory oxide-based material that is used in the purification method according to the invention is shaped. Any known method can be used to shape the porous refractory oxide-based material.

Advantageously, the adsorbent is used in the purification method according to the invention in the form of a stack of elementary particles that are in dissociated form or in the form of one or more multi-canal monoliths that are installed in a series or in parallel.

In the case where the adsorbent is used in the form of a stack of dissociated elementary particles, it comes in the form of balls, multilobed cylinders, preferably with between 2 and 5 lobes or in the form of rings, hollow cylinders, hollow rings, Raschig rings, serrated hollow cylinders, crenellated hollow cylinders, barrow wheels, berl saddles, or multi-hole cylinders, by themselves or in a mixture.

In the case where the adsorbent is used in the form of one or more multi-canal monoliths that are installed in series or in parallel, said adsorbent preferably comes in the form of a multi-canal monolith of the honeycomb type, where the canals can be square, hexagonal, circular, or oval in cross-section. The surfaces of the canals of the monolith can be smooth, fluted, or rough in order to promote close contact between the fluid to be treated and the surfaces of the canals of the monolith. The channel density can preferably vary from 5 to 400 cpsi (cpsi=canal per square inch) (respectively approximately 0.8 to approximately 62.0 canals per $cm^2$). Alternatively, the monolith can be composed of ceramic foam. The pore density of the ceramic foam is between 10 and 60 ppi and in a preferred manner between 10 and 30 ppi (ppi=pores per inch) (respectively between approximately 3.9 and approximately 23.6 pores per cm and in a preferred manner between approximately 3.9 and approximately 11.8 pores per cm).

The cross-section of the monolith should be equal to the internal cross-section of the reactor that contains the adsorbent bed in order to force all of the flow that is to be treated to circulate inside the canals of the monolith.

Advantageously, the fixed bed can comprise adsorbents that exhibit one or more types of shaping. The adsorbent that comprises the porous refractory oxide-based material can be used by itself or in a mixture with one or more other adsorbent(s).

It is particularly advantageous to stack different adsorbents, in particular those of different types and/or shaping, in at least two different fixed beds of variable height, where the adsorbents have the lowest drain rate, with the drain rate being defined as the ratio of the difference between the reactor volume and the volume of solid compared to the reactor volume (i.e., that which has the lowest volume filled by the adsorbent in question relative to the volume of the reactor), which is preferably used in the first fixed bed(s), at the inlet to the reactor, in order to perform a kind of filtering of the feedstock during its travel in the bed(s). Different adsorbents can also be mixed inside the same bed.

According to one embodiment of the invention, the adsorbent can be activated, especially in situ, just before its first use in the method according to the invention, according to any one of the methods known to one skilled in the art. Advantageously, the activation is accomplished by running a gas that is heated to between 100 and 500° C. The gas that is used can be a combustion gas, air, or nitrogen. Preferably, the activation gas is nitrogen.

Step b)

In accordance with the invention, the method for purifying the olefinic feedstock, in particular the step for simultaneously eliminating isobutanal and ethanol, operates at a temperature of between 0 and 200° C., preferably between 10 and 100° C., and preferably between 20 and 60° C., for example at 30° C., at a pressure of between 0.1 and 10 MPa and preferably between 0.3 and 5 MPa, and with an hourly volumetric flow rate (VVH) of said feedstock on said fixed bed of between 0.1 and 10 $h^{-1}$ and preferably between 0.2 and 5 $h^{-1}$.

Under these conditions and because of the specific adsorbent that is used in the purification method according to the invention, the adsorption of aldehydes and alcohols, in particular isobutanal and ethanol, is observed on the surface of the adsorbent at satisfactory rates. The method of purification according to the invention, due in particular to the specific adsorbent that is used under the particular conditions as defined here, makes it possible advantageously to capture the isobutanal and ethanol in the stream to be treated and to produce a stream at the outlet that has isobutanal and ethanol contents that are lower than the contents of the initial stream or even to eliminate the isobutanal and ethanol completely. In particular, the contents, by mass or molar, of isobutanal and ethanol in the effluent after treatment can be reduced by at least 90%, preferably at least 95%, and more preferably at least 99% relative to the corresponding contents in the olefinic feedstock before treatment.

According to a preferred embodiment of this invention, the purification of the olefinic feedstock, in particular the simultaneous elimination of isobutanal and ethanol, is done in a reactor that comprises multiple fixed beds that are arranged in parallel and that can be shuffled. Thus, it is possible to take out one of the guard beds for purposes of regeneration when the adsorbent(s) that comprises (comprise) it is (are) saturated with impurities, where this is done without shutting down the flow of the feedstock and thus without shutting down production.

Several options can be envisioned for the regeneration phase of the saturated fixed bed or guard bed.

According to a first embodiment, the saturated guard bed can be removed from the reactor. In this case, it is possible advantageously to eliminate the liquid, for example, by stripping, and then the solid, and to clean this part of the reactor. Recharging can advantageously be done with a new adsorbent charge or with the old adsorbent charge regenerated by, for example, running a solvent at between 30 and 200° C. or by burning, before putting this part back into the reactor.

According to a second embodiment, the regeneration of the saturated adsorbent bed can advantageously be done by rinsing on line with a solvent in co-current or counter-current in order to desorb the impurities that are adsorbed in the adsorption step. The solvent is advantageously a light hydrocarbon that is selected from among pentane, heptane, or hexane. According to one embodiment of the invention, the solvent can be heated to a temperature of between 30 and 350° C. The pressure is between 0.1 and 10 MPa and preferably between 0.3 and 5 MPa. With the impurities that are adsorbed during the adsorption phase and are extracted during this adsorbent regeneration being separated from the regeneration solvent at the reactor outlet, the solvent is advantageously recycled into the reactor to continue the regeneration.

According to a third embodiment, the phase of regeneration of the impurity-saturated guard bed is advantageously done by running a gas at between 180 and 500° C. The gas that is used can be a combustion gas, air, or nitrogen. The regeneration gas is preferably nitrogen. According to one version of the invention, the regeneration gas can contain water, between several ppm by volume and 40% by volume of water, preferably between 0.1 and 20% by volume, and in an even more preferred manner between 0.1 and 10% by volume.

Preferably, the regeneration of the adsorbent is done in situ. In an even more preferred manner, the regeneration of the adsorption is done in situ with a hot gas.

In the case where the purification according to the invention is carried out in a shuffling fixed bed with at least one adsorbent that comprises a porous refractory oxide-based material, the shuffling is advantageously done when the content of oxygenated hydrocarbon impurities in the butene mixture, after running over the adsorbent that comprises at least one refractory oxide-based material, is greater than 10 ppm by mass, in a preferred manner greater than 5 ppm by mass, and in an even more preferred manner greater than 1 ppm by mass.

Preferably, said method for purifying olefins according to the invention is used upstream from any method or any step for olefin transformation. In a preferred embodiment, said purification method can be placed upstream from a method for metathesis of said olefins. In the case where said purification method is placed upstream from a metathesis method, the purified olefin mixture constitutes the feedstock of the metathesis method.

The examples below are presented by way of illustration and are not limiting.

BRIEF DESCRIPTION OF THE DRAWINGS

FIG. 1 presents the breakthrough curves of ethanol and isobutanal that were obtained during the co-adsorption test on the adsorbent prepared in Example A and under the conditions of Test 2 of Table 1.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 17/62.091, filed Dec. 13, 2017, are incorporated by reference herein.

EXAMPLES

In Examples B and D below, the olefinic feedstock was first stripped with nitrogen and then run over a sieve 3A. At the end of this pretreatment, the water and acetone contents of the feedstock are verified by, respectively, the method of Karl Fischer and gas-phase chromatography according to the UOP 960 method. The olefinic feedstock that is tested in Examples B and D no longer contains either water or acetone.

In Example C below, the olefinic feedstock was first run over a sieve 3A. An analysis by the method of Karl Fischer shows that, at the end of this pretreatment, the olefinic feedstock that is tested in Example C no longer contains water.

Example A. Preparation of an Adsorbent According to the Invention

The adsorbent is prepared by dry impregnation of a material such as flash alumina, which is shaped by granulation, using a solution of NaOH.

The alumina selected has a pore volume of 0.5 ml/g, a macropore volume of 0.1 ml/g, a specific surface area of 341 m²/g, and a sodium content before impregnation of 1,948 ppm by mass.

The specific surface area is determined by the B.E.T. method according to the Standard ASTM D3663. The total pore volume and the macropore volume are determined by application of the Standard ASTM D4284 by mercury intrusion measurement with a wetting angle of 140°, using a device such as the Autopore III™ model of the Micromeritics™ brand. The sodium content is measured by atomic absorption spectroscopy.

Impregnation is done as follows:

a) Preparation of 50 mL of a soda (NaOH) solution by dissolving 8.84 g of NaOH in 50 g of water;

b) Streaming, drop by drop using a burette, of 5 mL of the soda solution prepared according to Step a), onto 10 g of flash alumina that has been placed in advance in a rotating receptacle (impregnation phase);

c) Curing of the impregnated material in a closed water-saturated container at 20° C. for 3 hours;

d) Drying of the solid under dry air at 90° C. for 3 hours in an oven;

e) Calcining of the solid under dry air at 350° C. for 1 hour.

After impregnation, the sodium content as measured by atomic absorption spectroscopy is 4.1% by weight relative to the total weight of the adsorbent.

The adsorbent A that is prepared is white in color.

Example B. Co-Adsorption of Isobutanal and Ethanol and Production of Purified Butenes The adsorbent A, prepared in accordance with Example A, is tested in a fixed-bed reactor at 30° C. under 0.8 MPa. The feedstock is composed of 80% n-butene and 20% isobutene and comprises isobutanal and ethanol in variable proportions (see Table 1, Tests 1 to 3).

In parallel, an adsorbent of the NaY zeolite type from Zeolyst, white, shaped by pelletizing and crushing, is tested under the same conditions. The feedstock is composed of 80% n-butene and 20% isobutene and comprises isobutanal and ethanol at levels of 3,023 and 963 ppm by mass, respectively.

The fixed bed of adsorbent is first activated at 290° C. under $N_2$ for 12 hours and is then filled with butane at 30° C. under 0.8 MPa. The feedstock is then injected into the reactor at a flow rate of 0.5 ml/min continuously, i.e., an hourly volumetric flow rate of 0.5 $h^{-1}$.

The tracking of the concentrations of isobutanal and ethanol at the reactor outlet is done by means of gas-phase chromatography analysis on a microGC 4900 from Varian.

The test is halted when the concentrations of isobutanal and ethanol impurities in the discharge effluent are the same as those in the entry feedstock.

At the end of the test, the adsorbent A and the NaY zeolite are white in color.

The capture capacities of the adsorbents at saturation with regard to isobutanal and ethanol are calculated by means of a material balance between what enters the column and what leaves it. These capture capacities, expressed in g of the impurity in question (isobutanal or ethanol) for 100 g of adsorbent, are recorded in Table 1, along with the feedstock concentrations of isobutanal and ethanol, expressed in ppm by mass and their molar ratio.

TABLE 1

Quantities of Isobutanal and Ethanol in the Feedstock and Quantities
Adsorbed by Adsorbent A (Sodium-Doped Alumina) and by the NaY Zeolite

| Adsorbent | Test | [Isobutanal] (ppm by Mass) | [Ethanol] (ppm by Mass) | Molar Ratio of Isobutanal/Ethanol | $q_{ads\_isobutanal}$ (g/100 g) | $q_{ads\_ethanol}$ (g/100 g) |
|---|---|---|---|---|---|---|
| A (According to the Invention) | 1 | 1796 | 330 | 3.5 | 6.4 | 2.2 |
| | 2 | 644 | 410 | 1 | 4.3 | 3.4 |
| | 3 | 9 | 30 | 0.2 | 2.9 | 5.2 |
| NaY (Comparitive Test) | 4 | 13,023 | 963 | 2 | 1.4 | 18.4 |

The adsorbent A has significant capture capacities for isobutanal and ethanol, and these capacities are of the same order of magnitude regardless of the concentrations and proportions of isobutanal and ethanol in the feedstock. Even in the case of a feedstock with an excess of ethanol relative to isobutanal (isobutanal/ethanol molar ratio at 0.2), the capture capacity of adsorbent A for isobutanal remains high (2.9 g for 100 g of adsorbent).

By contrast, the NaY zeolite exhibits a low capture capacity for isobutanal (1.4 g for 100 g of adsorbent) when the feedstock contains ethanol, even with an excess of isobutanal (2× more isobutanal than ethanol). This adsorbent is thus not suitable for ensuring eliminating isobutanal and ethanol jointly.

The breakthrough curves of ethanol and isobutanal on the adsorbent as prepared in Example A, which were obtained during the ethanol/isobutanal co-adsorption test at molar iso-concentration in the feedstock (Test 2 of Table 1), are depicted in FIG. 1.

As shown in FIG. 1, it appears that the method according to the invention, which is carried out on a bed of adsorbent A (sodium-impregnated alumina) and at 30° C., makes it possible to obtain isobutanal and ethanol contents in the reactor output effluent that are less than 1 ppm by mass. As a matter of fact, the concentrations of isobutanal and ethanol in the reactor output effluent are below the detection limit of 1 ppm by mass for 75 and 105 minutes, respectively, for isobutanal and ethanol.

Example C. Co-Adsorption of Isobutanal, Ethanol, and Acetone and Production of Purified Butenes—Comparative Example A test similar to that of Example B is carried out with a feedstock that is composed of 80% n-butene and 20% isobutene and that comprises a mixture of isobutanal (642 ppm by mass), ethanol (413 ppm by mass), and acetone (519 ppm by mass).

After the test, the adsorbent A is removed. It is orange in color.

The comparison of the appearances of the adsorbent A after the tests, between Example B (feedstock comprising isobutanal and ethanol) and Example C (feedstock comprising isobutanal, ethanol, and acetone), shows that the presence of acetone in the feedstock has caused degradation thereof during the course of the test. A feedstock that contains acetone thus has to be pretreated in order to eliminate at least the acetone, before the step of joint elimination of isobutanal and ethanol on an adsorbent according to the invention is carried out.

Example D. Regenerability of the Adsorbent and Cycling

The adsorbent A, as prepared according to Example A, is tested on a fixed bed in a column at 30° C. under 0.8 MPa. The feedstock is composed of 80% n-butene and 20% isobutene and comprises 644 ppm by mass of isobutanal and 410 ppm by mass of ethanol. The operating conditions tracked are those described in Example B.

The isobutanal and ethanol concentrations in the output effluent are tracked by gas-phase chromatographic analysis on a microGC 4900 from Varian.

When the output composition becomes identical to the input composition, the adsorbent is considered saturated. The flow of the feedstock is halted, and the adsorbent is regenerated under a stream of nitrogen at atmospheric pressure at 290° C. at 20 NL/h. When the concentrations of isobutanal and ethanol at the output of the column become zero, regeneration is considered completed. The stream of nitrogen is replaced by a flow of feedstock identical to that of the first cycle, so as to initiate a second adsorption cycle. The concentrations of isobutanal and ethanol at the reactor output are tracked as above by gas-phase chromatographic analysis on a microGC 4900. When the output composition becomes identical to the input composition, the column is again subjected to a stream of nitrogen at atmospheric pressure at 290° C. Four cycles of adsorption/regeneration are strung together. The capture capacities for isobutanal and ethanol are recorded in Table 2.

TABLE 2

Quantities of Isobutanal and Ethanol Adsorbed by Adsorbent A after Each Adsorption/Desorption Cycle

| Cycle | $q_{ads\_isobutanal}$ (g/100 g) | $q_{ads\_ethanol}$ (g/100 g) |
|---|---|---|
| 1 | 4.3 | 3.4 |
| 2 | 3.5 | 3.0 |
| 3 | 2.5 | 2.4 |
| 4 | 1.8 | 2.2 |
| 5 | 1.6 | 2.1 |

The capture capacities for isobutanal and ethanol remain satisfactory after 5 cycles. The adsorbent A is thus always able to eliminate isobutanal and ethanol jointly after 5 cycles.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method for purifying an olefinic feedstock that comprises olefins with 4 carbon atoms and impurities including isobutanal, ethanol, and acetone, wherein said method comprises:
   a) pretreatment that comprises at least one acetone elimination; and
   b) simultaneously eliminating isobutanal and ethanol by running the pretreated feedstock obtained from a) over at least one fixed bed with at least one adsorbent that comprises at least one porous refractory oxide-based material,
   wherein b) operates at a temperature of between 0 and 200° C., at a pressure of 0.1 to 10 MPa, and with an hourly volumetric flow rate (VVH) of the pretreated feedstock obtained from a) over the fixed bed of between 0.1 and 10 h$^{-1}$.

2. The method in accordance with claim 1, wherein said olefinic feedstock is produced from the dehydration of isobutanol or a mixture of butanol isomers that comprises isobutanol.

3. The method in accordance with claim 1, wherein the pretreatment also comprises eliminating water that is present in said olefinic feedstock, wherein acetone-elimination and water-elimination are carried out simultaneously or successively.

4. The method in accordance with claim 1, wherein the porous refractory oxide-based material is: alumina, silica, titanium oxide, zirconium oxide, magnesium oxide, or mixtures thereof.

5. The method in accordance with claim 1, wherein the porous refractory oxide-based material is based on alumina.

6. The method in accordance with claim 1, wherein the porous refractory oxide-based material has a macropore volume, defined as a cumulative volume of the pores that are greater than 50 nm in diameter, as measured by mercury intrusion, of greater than or equal to 0.01 ml/g, a total pore volume, as measured by mercury intrusion according to the Standard ASTM D4284 with a wetting angle of 140°, greater than or equal to 0.05 ml/g, and a specific surface area, expressed in terms of $S_{BET}$ and measured by the B.E.T. method in accordance with the Standard ASTM D3663, between 30 m$^2$/g and 400 m$^2$/g.

7. The method in accordance with claim 1, wherein the porous refractory oxide-based material is impregnated with one or more alkaline or alkaline-earth cations.

8. The method in accordance with claim 7, wherein the cation is a cation of sodium, potassium, magnesium, or calcium.

9. The method in accordance with claim 7, wherein the porous refractory oxide-based material is impregnated with one or more alkaline or alkaline-earth cations at a level from 0.2 to 40% by weight, relative to the total weight of the adsorbent after impregnation.

10. The method in accordance with claim 1, wherein b) operates at a temperature between 20 and 60° C.

11. The method in accordance with claim 1, wherein b) operates at a pressure between 0.3 and 5 MPa.

12. The method in accordance with claim 1, wherein b) is carried out such that the hourly volumetric flow rate (VVH) of said feedstock on said fixed bed is between 0.2 and 5 h$^{-1}$.

13. The method in accordance with claim 1, wherein b) is carried out in a reactor that comprises multiple fixed beds that are arranged in parallel and that can be shuffled.

14. A method for transforming olefins, comprising purification of the olefinic feedstock in accordance with claim 1 upstream from a metathesis method.

* * * * *